United States Patent [19]

McCooeye et al.

[11] Patent Number: 5,459,533
[45] Date of Patent: Oct. 17, 1995

[54] DEFOGGING EYE WEAR

[75] Inventors: Donald E. McCooeye; J. Albert Bingham, both of Nepean, Canada

[73] Assignee: See Clear Eyewear Inc., Ottawa, Canada

[21] Appl. No.: 150,808

[22] Filed: Nov. 12, 1993

[51] Int. Cl.$^6$ .................................................. G02C 11/08
[52] U.S. Cl. ............................................. 351/62; 351/41
[58] Field of Search .............................. 351/62, 158, 41, 351/43, 154; 2/435, 426

[56] References Cited

U.S. PATENT DOCUMENTS

| | | |
|---|---|---|
| 3,160,736 | 12/1964 | Catterson . |
| 3,530,275 | 9/1970 | Rust . |
| 3,597,586 | 8/1971 | Rebovich . |
| 3,624,347 | 11/1971 | Todd et al. . |
| 3,686,473 | 8/1972 | Shim et al. . |
| 3,790,748 | 2/1974 | Van Laethem et al. . |
| 3,839,620 | 10/1974 | Seibel et al. . |
| 3,887,788 | 6/1975 | Seibel et al. . |
| 4,037,079 | 7/1977 | Armbruster . |
| 4,060,712 | 11/1977 | Chang . |
| 4,071,736 | 1/1978 | Kamerling . |
| 4,209,234 | 6/1980 | McCooeye . |
| 4,237,366 | 12/1980 | Berg . |
| 4,278,870 | 7/1981 | Carleton et al. . |
| 4,352,006 | 9/1982 | Zega . |
| 4,410,790 | 10/1983 | Berg et al. . |
| 4,527,047 | 7/1985 | Seitz . |
| 4,665,304 | 5/1987 | Spencer . |
| 4,701,594 | 10/1987 | Powell . |
| 4,868,929 | 9/1989 | Curcio . |
| 4,882,467 | 11/1989 | Dimick . |
| 4,933,533 | 6/1990 | Simpson . |
| 4,942,286 | 7/1990 | Monter et al. . |
| 4,942,629 | 7/1990 | Stadlmann . |
| 4,956,542 | 9/1990 | Prosser . |
| 5,015,824 | 5/1991 | Monter et al. . |
| 5,079,406 | 1/1992 | Nagy . |
| 5,083,009 | 1/1992 | Reiser et al. . |
| 5,149,942 | 9/1992 | Garrett . |
| 5,155,334 | 10/1992 | Marstiller et al. . |
| 5,198,639 | 3/1993 | Smuckler . |
| 5,206,482 | 4/1993 | Smuckler . |

FOREIGN PATENT DOCUMENTS

| | | |
|---|---|---|
| 981319 | 1/1976 | Canada . |
| 1094785 | 2/1984 | Canada . |
| 2021937 | 1/1991 | Canada . |

*Primary Examiner*—William L. Sikes
*Assistant Examiner*—Hung Xuan Dang
*Attorney, Agent, or Firm*—Kent & Edgar

[57] ABSTRACT

An eye wear device comprising a frame and lens means supported by the frame to be positioned in front of a wearer's eyes. The improvement characterized in that the lens means is coated with an electrically conductive heat generating layer to be positioned in the wearer's field of vision when the eye wear is worn, and of sufficient resistance to produce enough heat to remove moisture build-up on the lens means. Contacts are provided at either end of the layer, each contact electrically associated with the layer, an electronic moisture sensor means associated with the lens means to detect a moisture build-up on the lens means, circuitry associated with the contacts and moisture sensor, in operation to be electrically connected to a power source, microchip means electrically associated with the circuitry and moisture sensor, and arranged to permit a flow of current from the power source across the layer when moisture builds up on the lens to a predetermined degree, and to stop that flow of current across the layer when the moisture level on the lens falls below a predetermined degree.

14 Claims, 2 Drawing Sheets

DEFOGGING EYE WEAR

BACKGROUND OF THE INVENTION

1. Field of the Invention

The present invention relates to eye wear, and more particularly relates to glasses and ski goggles of the type that remove frost and fog which may gather thereon.

2. Description of the Prior Art

In McCooeye U.S. Pat. No. 4,209,234, issued Jun. 24, 1980, a defogging system for eye glasses was described and illustrated in which lenses are coated with a conductive transparent film, the film being in electrical contact with electrical circuitry, and circuitry and a power source in the rims of the glasses, so that current is passed through the transparent film to defog the lenses, as dictated by a thermostat controlled switch in the circuitry. Such a system, while useful under certain conditions, responds to temperature, and not necessarily to moisture, conditions on the lenses of the eye glasses.

U.S. Pat. No. 4,868,929 of Curcio issued Sep. 26, 1989 teaches defogging ski goggles which are electrically heated using a fine resistance wire grid extending across the lens.

Other patents of general background interest include U.S. Pat. No. 4,942,629 of Stadlmann issued Jul. 24, 1990 relating to a solar heated ski goggles lens and, relating to condensation controls for mirrors, Canadian Patent No. 981,319 of Glaverbel-Mecaniver issued Jan. 6, 1976; Canadian Patent No. 1,094,785 of Britax (Wingard) Limited issued Feb. 3, 1984; U.S. Pat. No. 3,530,275 of Rust issued Sep. 22, 1970; Canadian Patent Application Serial No. 2,021,937 of Colin Terry filed Jan. 27, 1991; U.S. Pat. No. 3,160,736 of Catterson issued Dec. 8, 1964; U.S. Pat. No. 3,597,586 of Rebovich issued Aug. 3, 1971; U.S. Pat. No. 3,624,347 of Todd et al issued Nov. 30, 1971; U.S. Pat. No. 3,686,473 of Shirn et al issued Aug. 22, 1972; U.S. Pat. No. 3,790,748 of Van Laethem et al issued Feb. 5, 1974; U.S. Pat. No. 3,839,620 of Seibel et al issued Oct. 1, 1974; U.S. Pat. No. 3,887,788 of Seibel et al issued Jun. 3, 1975; U.S. Pat. No. 4,037,079 of Armbruster issued Jul. 19, 1977; U.S. Pat. No. 4,060,712 of Chang issued Nov. 29, 1977; U.S. Pat. No. 4,071,736 of Kamerling issued Jan. 31, 1978; U.S. Pat. No. 4,237,366 of Berg issued Dec. 2, 1980; U.S. Pat. No. 4,278,870 of Carleton et al issued Jul. 14, 1981; U.S. Pat. No. 4,352,006 of Zega issued Sep. 28, 1982; U.S. Pat. No. 4,410,790 of Berg et al issued Oct. 18, 1983; U.S. Pat. No. 4,527,047 of Seitz issued Jul. 2, 1985; U.S. Pat. No. 4,665,304 of Spencer issued May 12, 1987; U.S. Pat. No. 4,701,594 of Powell issued Oct. 20, 1987; U.S. Pat. No. 4,882,467 of Dimick issued Nov. 21, 1989; U.S. Pat. No. 4,933,533 of Simpson issued Jun. 12, 1990; U.S. Pat. No. 4,942,286 of Monter et al issued Jul. 17, 1990; U.S. Pat. No. 4,956,542 of Prosser issued Sep. 11, 1990; U.S. Pat. No. 5,015,824 of Monter et al issued May 14, 1991; U.S. Pat. No. 5,079,406 of Nagy issued Jan. 7, 1992; U.S. Pat. No. 5,083,009 of Reiser et al issued Jan. 21, 1992; U.S. Pat. No. 5,149,942 of Garrett issued Sep. 22, 1992; U.S. Pat. No. 5,155,334 of Marstiller et al issued Oct. 13, 1992; U.S. Pat. No. 5,198,639 of Smuckler issued Mar. 30, 1993; U.S. Pat. No. 5,206,482 of Smuckler issued Apr. 27, 1993.

SUMMARY OF THE INVENTION

It is an object of the present invention to provide an improved construction for defogging of eye wear, such as ski goggles and eye glasses, which overcomes the shortcomings of known prior art devices.

It is a further object of the present invention to provide such a device that is economical to construct and effective in operation.

In accordance with the present invention, there is provided for an eye wear device comprising a frame and lens means supported by the frame to be positioned in front of a wearer's eyes, an improvement characterized in that the lens means is coated with an electrically conductive heat generating transparent layer to be positioned in the wearer's field of vision when the eye wear is worn, and of sufficient resistance to produce enough heat to remove moisture build-up on the lens means. Contacts are provided at either end of the layer, each contact electrically associated with the layer. An electronic moisture sensor means is associated with the lens means to detect a moisture build-up on the lens means. Circuitry is associated with the contacts and moisture sensor, in operation to be electrically connected to a power source. Microchip means are electrically associated with the circuitry and moisture sensor, and arranged to permit a flow of current from the power source across the layer when moisture builds up on the lens to a predetermined degree, and to stop that flow of current across the layer when the moisture level on the lens falls below a predetermined degree.

In one embodiment of the present invention, the layer is a thin layer of chrome and the contacts are thicker layers of chrome. The moisture sensor comprises a metallic strip on the lens means spaced from the electrically conductive layer and electrically associated with the power source, a current measuring amplifier and a comparator, these components arranged so that when the resistance on the lens means falls below a predetermined level, as measured by the current flow between the metallic strip and the electrically conductive layer, as a result of moisture build-up on the lens means to a predetermined degree, the comparator activates a switch means to cause high current flow between the contacts across the electrically conductive layer until the current flow between the sensor and the electrically conductive layer falls below a predetermined level.

When eye glasses or ski goggles or the like are of a construction in accordance with the present invention, and the circuitry connected to an appropriate power source, current will not flow through the electrically conductive heat generating layer or layers between the contacts until such time as the moisture sensor indicates a sufficient build-up of moisture on the lens or lenses to warrant current flow.

Eye wear may be constructed in accordance with the invention which is both lightweight and attractive in appearance, yet effective in providing clear vision through the lenses, unobstructed by wires or the like.

BRIEF DESCRIPTION OF THE DRAWINGS

These and other objects and advantages of the invention will become apparent upon reading the following detailed description and upon referring to the drawings in which.

Figure 1:
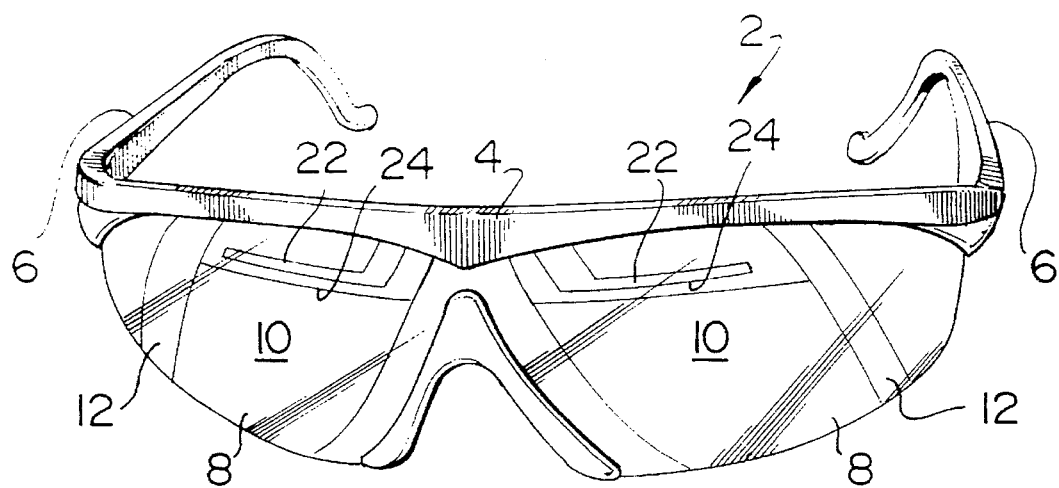
FIG. 1 is a perspective view of a pair of eye glass protective lenses embodying the present invention.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the drawings, similar features have been given similar reference numerals.

Figure 2:
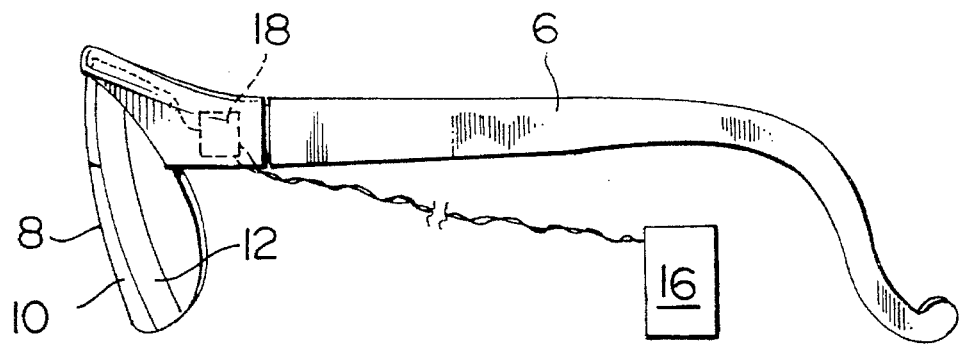
FIG. 2 is a side view of a pair of eye glass protective lenses in accordance with the present invention.
Figure 4:
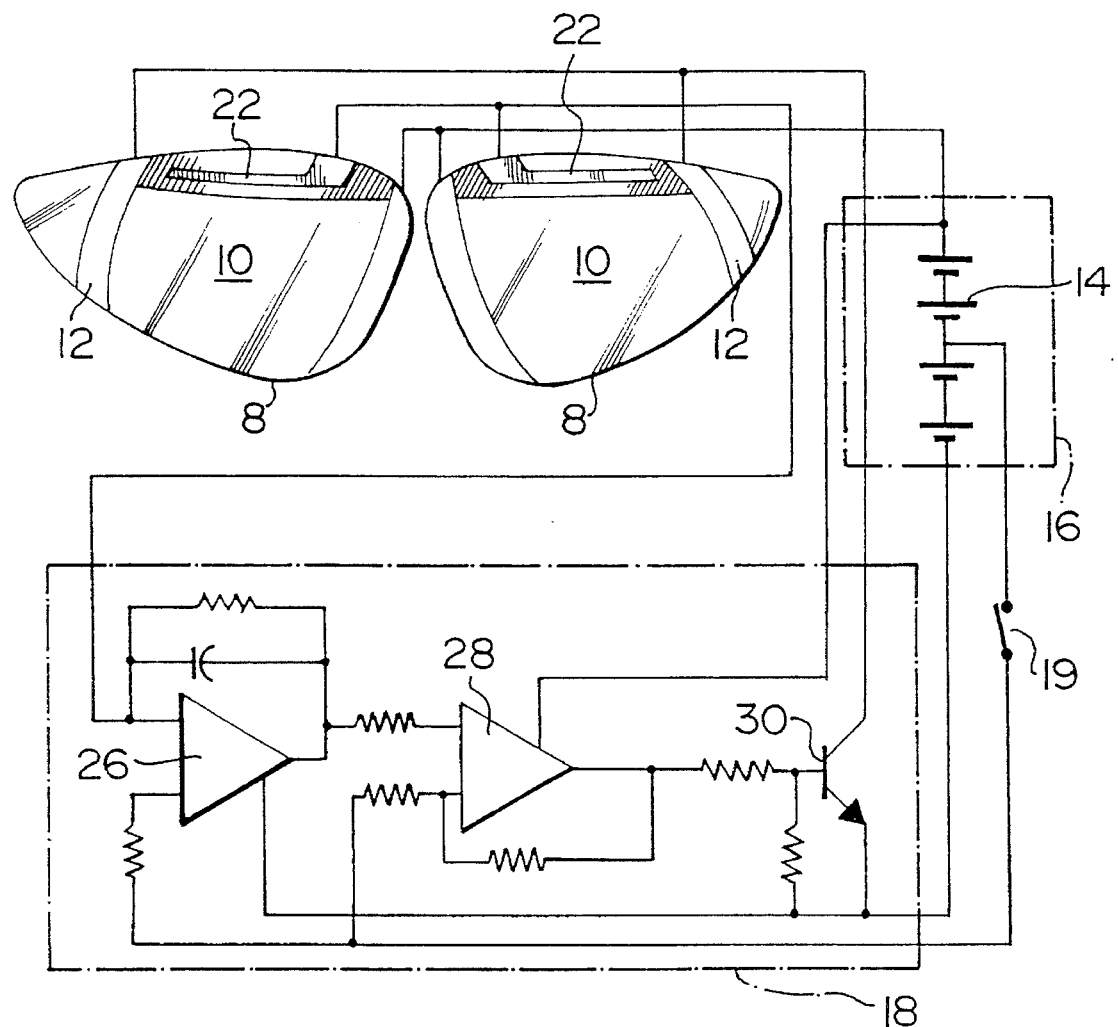
FIG. 4 is a perspective view of ski goggles embodying the present invention.

Turning to FIGS. 1 and 2 there is shown a ski goggles device 2 comprising a frame 4 extending between a pair of temples 6. Frame 4 supports a pair of lenses 8 so as to be positioned in front of the wearer's eyes during use. The lenses 8 are each coated with an electrically conductive heat generating transparent layer 10 of any appropriate material. For example, in the present case, chrome has been found to be suitable. Alternatively, a thin layer of chrome with a further, thin layer of silver, and a transparent coating over the silver to prevent oxidation, would also appear to be suitable. A thin layer or layers of such materials, so as not to obstruct the wearer's vision, are placed on the lenses. The layers are preferably placed on the inside of the lenses, but may alternatively be placed on the outside and/or or the inside, depending upon the intended use of the glasses, and the likelihood of conditions developing which would fog-up the lenses on either the inside, outside, or both. In the illustrated embodiment, the layer is of parallelogram shape for reasons which will be explained in more details subsequently. To either side of the parallelogram shape of layer 10 is a contact 12, which contact may for example be a thicker layer of chrome. As can be seen in FIG. 4, appropriate circuitry is provided from contacts 12 to a power source 14 which may for example be a remote portable power pack 16 as illustrated (shown schematically and in phantom in FIG. 2), or alternatively a suitable solar or other battery means positioned in frame 4 or temple 6, through a microchip 18. An on-off switch 19 may be provided in the circuitry. An electronic moisture sensor means 20 is associated with each of the lenses 8 and microchip 18, to detect a moisture build-up on the lenses 8. The microchip 18 and moisture sensor 20 are arranged so that in 10 operation, when power source 14 is connected to the circuitry, a flow of current from power source 14 is permitted across the layers 10, between contacts 12, when moisture builds up on the lenses to a predetermined degree, and to stop that flow of current across layers 10 when the moisture level lenses 8 falls below a predetermined degree. For example the resistance provided by layers 10 may be in the order of 1000 to 1200 ohms per square inch and the power source 14 may be such as to provide 12 to 30 volts of power between adjacent co-operating contacts 12 (depending upon the layer material(s) used.

More particularly, as can be seen in FIG. 2, moisture sensor 20 comprises a metallic strip 22 on each of the lenses 8, spaced from an adjacent edge 24 of electrically conductive layers 10. This metallic strip 22 is, through appropriate circuitry, associated with the power source 14. A current measuring amplifier 26 and a comparator 28 are incorporated in microchip 18 as part of sensor 20, and arranged so that when the resistance on the lenses falls below a predetermined level, as measured by the current flow between the strip 22 and the associated edge 24 of the adjacent electrically conductive layer 10, as a result of moisture build-up on the lenses 8 to a predetermined degree, the comparator 28 activates a transistor switch 30 to cause the current flow between the corresponding contacts across electrically conductive layer 10 therebetween, until the current flow between the strip 22 and the electrically conductive layer 10 falls below a predetermined level. The parallelogram shape of layer 10 is ideal since, in the illustrated embodiment, it will be understood that current flow will commence first across the area adjacent upper edge 24, that being the area where moisture build-up, being frost or fog, usually occurs first and is thickest.

Figure 3:
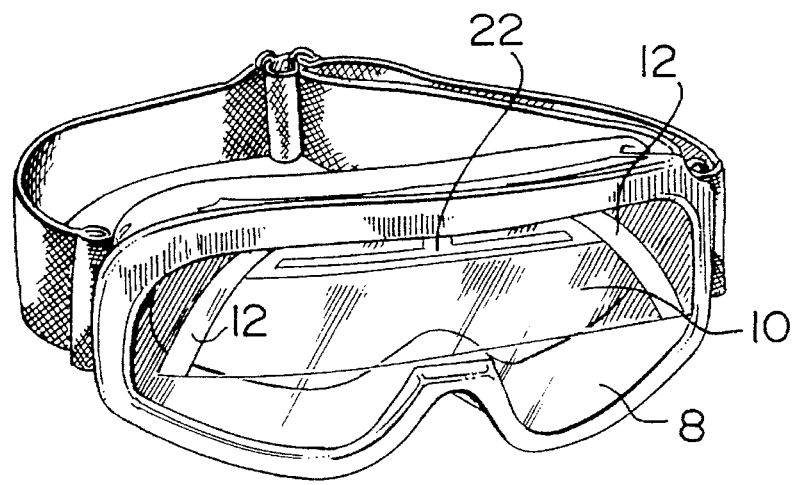
FIG. 3 is a schematic view of a pair of eye glass lenses and associated circuitry in accordance with the present invention.

In FIG. 3, ski goggles embodying the present invention but having a single layer 10 of trapezoidal shape across the field of vision of the wearer, between a pair of contacts 12, is illustrated.

It will be understood that because a discrete area of heat generating material is placed on the lenses by way of layers 10, a predetermined, but small area where defogging of the lens can take place is provided. In this manner the power requirements for operation of the device are kept to a minimum.

Thus it is apparent that there has been provided a construction of defogging eye wear in accordance with the invention that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What we claimed as our invention:

1. In an eye wear device comprising a frame and lens means supported by the frame to be positioned in front of a wearer's eyes, the improvement characterized in that the lens means is coated with an electrically conductive heat generating transparent layer to be positioned in the wearer's field of vision when the eye wear is worn, and of sufficient resistance to produce enough heat to remove moisture build-up on the lens means, a contact at either end of the layer, each contract electrically associated with the layer, an electronic moisture sensor means associated with the lens means to detect a moisture build-up on the lens means, the moisture sensor means comprising a metallic strip on the lens means spaced from the electrically conductive layer, the contacts and moisture sensor electrically connected to a power source, and microchip means comprising a current measuring amplifier and a comparator, these components arranged so that when the resistance on the lens means falls below a predetermined level, as measured by the current flow between the metallic strip and the electrically conductive layer, as a result of moisture build-up on the lens means to a predetermined degree, the comparator activates a switch means to cause high current flow between the contacts across the electrically conductive layer until the current flow between the sensor and the electrically conductive layer falls below said predetermined level, when the switch means is deactivated and the current flow is stopped.

2. A device according to claim 1 wherein the resistance of the layer is about 1000 to 1200 ohms per square inch.

3. A device according to claim 2 in combination with a power source, the device and power source arranged to generate from between about 12 to 30 volts of power across between the contacts.

4. A device according to claim 1 wherein the layer is a thin layer of chrome.

5. A device according to claim 4 wherein the contacts are thicker layers of chrome.

6. A device according to claim 4 wherein the layer of chrome is covered with a thin layer of silver.

7. A device according to claim 1 wherein the eye wear comprises ski goggles with a single lens.

8. A device according to claim 7 wherein the electrically conductive layer is of elongated parallelogram shape.

9. A device according to claim 1 wherein the eye wear comprises protective glasses with a pair of lens areas, one to be positioned before each eye, each lens area being coated with an electrically conductive heat generating layer and each having contacts electrically associated with the layer at either end.

10. A device according to claim 6 wherein the electrically conductive layer is of elongated parallelogram shape.

11. A device according to claim 9 wherein the microchip and circuitry are incorporated in the eye glass frame.

12. A device according to claim 1 wherein the electrically conductive layer is of elongated parallelogram shape.

13. A device according to claim 1 wherein the layer is a thin layer of chrome and wherein the contacts are thicker layers of chrome.

14. A device according to claim 13 wherein the eye wear comprises protective glasses with a pair of lens areas, one to be positioned before each eye, each lens area being coated with an electrically conductive heat generating layer and each having contacts electrically associated with the layer at either end.

* * * * *